United States Patent [19]

Langla et al.

[11] Patent Number: 5,057,312

[45] Date of Patent: Oct. 15, 1991

[54] ANHYDROUS NAIL VARNISHES

[75] Inventors: Bernard Langla, Paris; Jean Mondet, Drancy; Christos Papantoniou, Montmorency, all of France

[73] Assignee: L'Oreal, Paris, France

[21] Appl. No.: 208,052

[22] Filed: Jun. 17, 1988

[30] Foreign Application Priority Data

Jun. 19, 1987 [LU] Luxembourg ............................ 86924

[51] Int. Cl.$^5$ .............................................. A61K 31/78
[52] U.S. Cl. ......................................... 424/81; 424/61; 526/320
[58] Field of Search ...................... 424/61, 81; 526/320

[56] References Cited

U.S. PATENT DOCUMENTS 3,577,518  5/1971  Shepherd et al. .
3,749,769  7/1973  Sugiyama et al. ................... 424/61

FOREIGN PATENT DOCUMENTS 0085370  8/1983  European Pat. Off. .
0154679  9/1985  European Pat. Off. ............... 424/61
2009296  12/1970  Fed. Rep. of Germany .
2022299  6/1970  France .
859297  1/1961  United Kingdom ................ 526/320
2073229  10/1981  United Kingdom .

Primary Examiner—Lester L. Lee
Assistant Examiner—E. J. Kraus
Attorney, Agent, or Firm—Oliff & Berridge

[57] ABSTRACT

This nitrocellulose-free varnish contains at least one resin in a solvent system for varnishes, and is characterized in that the said resin is a copolymer containing units resulting from the copolymerization:

(1) of 20 to 70% of at least one alkyl acrylate or methacrylate of general formula:

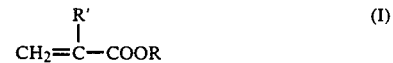

(I)

in which:
R' denotes a hydrogen atom or a methyl radical, and
R denotes a saturated, linear or branched hydrocarbon chain containing from 1 to 6 carbon atoms, and (2) of 30 to 80% of at least one hydroxyalkyl acrylate or methacrylate of general formula:

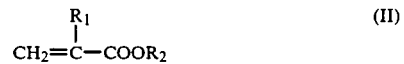

(II)

in which:
$R_1$ denotes a hydrogen atom or a methyl radical and $R_2$ denotes a linear or branched hydrocarbon chain containing from 2 to 4 carbon atoms and 1 or 2 hydroxyl(s), it being understood that the said copolymer cannot contain more than 30% of units derived from the copolymerization of an alkyl acrylate and/or a hydroxyalkyl acrylate, the viscosity of the copolymer at a concentration of 28% in ethyl acetate at 25° C. being higher than 0.1 Pa s.

9 Claims, No Drawings

ANHYDROUS NAIL VARNISHES

The present invention relates to manicure products, especially anhydrous nail varnishes which have good behaviour with time, good gloss and excellent adhesion to the nail keratin.

Recent studies on nail varnishes have been concerned essentially with the replacement of nitrocellulose and of "Santolite" (aryl sulphonamide formaldehyde resin) by certain copolymers.

French Patent No. 80/07,328 provides, for this purpose, copolymers resulting from the copolymerization of at least one unsaturated polar monomer, an alkyl methacrylate and an alkyl acrylate.

It has now just been found, quite surprisingly, that copolymers of this type made it possible not only to replace nitrocellulose, but also, in coloured nail varnishes, products which make it possible to prevent pigment sedimentation.

In fact, coloured nail varnishes contain pigments of inorganic or organic nature which tend to precipitate, so that, in order to prevent their sedimentation, it is necessary to make use of certain products, especially montmorillonite-type clays modified by an amine.

Among these montmorillonite-type clays, very particular mention must be made of those marketed by the National Lead Company under the names of "Bentone" and more particularly "Bentone 27" (or benzyldodecyldimethylammonium-montmorillonite) and "Bentone 38" (or dimethyldioctadecylammonium-montmorillonite).

In fact, these montmorillonite-type clays modified by an amine have the property of swelling under the effect of certain solvents such as, for example, toluene, and of imparting thixotropic properties to the varnish compositions, owing to their arrangement in space.

However, their use is not free from certain disadvantages in respect of the quality of the films obtained.

In fact, these clays have a tendency to make the films more matt and, additionally, require the use of agents capable of causing the clay to swell, these agents being orthophosphoric acid, metaphosphoric acid or citric acid.

It should be noted, furthermore, that the use of such acids is liable to cause the deterioration of certain coloured pigments.

Consequently, the present invention provides, in anhydrous nail varnishes, a particular class of copolymers permitting not only the complete replacement of nitrocellulose, but also a partial or complete replacement of the montmorillonite-type clays modified by an amine.

When compared with the state of the art, the invention thus provides a twin advantage, in the case of coloured nail varnishes, while endowing the varnishes with excellent properties in respect of the gloss of the film and of its adhesion to the nail keratin.

It has been noted furthermore, that the coloured or colourless films were much less sensitive to alcohols and to detergents.

The subject of the present invention, as a new industrial product, is an anhydrous nail varnish, free from nitrocellulose, containing at least one resin in a solvent system for varnishes, the said resin being a copolymer containing units resulting from the copolymerization:

(1) of 20 to 70% by weight of at least one alkyl acrylate or methacrylate of general formula:

$$CH_2=C(R')-COOR \quad (I)$$

in which:
R' denotes a hydrogen atom or a methyl radical and
R denotes a saturated, linear or branched hydrocarbon chain containing from 1 to 6 carbon atoms, and (2) of 30 to 80% by weight of at least one hydroxyalkyl acrylate or methacrylate of general formula:

$$CH_2=C(R_1)-COOR_2 \quad (II)$$

in which:
$R_1$ denotes a hydrogen atom or a methyl radical, and
$R_2$ denotes a linear or branched hydrocarbon chain containing from 2 to 4 carbon atoms and 1 or 2 hydroxyl(s), it being understood that the said copolymer cannot contain more than 30% of units derived from the copolymerization of an alkyl acrylate and/or of a hydroxyalkyl acrylate, the viscosity of the said copolymer at a concentration of 28% in ethyl acetate at 25° C. being higher than 0.1 Pa s, and preferably between 0.15 and 20 Pa s.

According to a preferred embodiment of the invention, the copolymer contains units resulting from the copolymerization:

(1) of 40 to 60% by weight of an alkyl acrylate or methacrylate of formula (I), and
(2) of 40 to 60% of a polar monomer of formula (II).

Among the alkyl acrylates and methacrylates of formula (I), particular mention may be made of methyl, ethyl, propyl, isopropyl, butyl, tert-butyl and hexyl acrylates and methacrylates.

Among the hydroxyalkyl acrylates and methacrylates of formula (II), particular mention may be made of 2-hydroxypropyl, 2-hydroxy-1-methylethyl, 2,3-dihydroxypropyl, 2-hydroxyethyl, 3-hydroxypropyl or 4-hydroxybutyl acrylates and methacrylates.

The copolymers of the nail varnishes according to the invention generally have a molecular weight of between 20,000, and 1,000,000 and preferably between 30,000 and 200,000.

Among the copolymers according to the invention which are especially preferred, the following may be mentioned in particular:
butyl methacrylate - 2-hydroxypropyl methacrylate,
butyl methacrylate - (1-methyl-2-hydroxy)ethyl methacrylate,
butyl methacrylate - methyl methacrylate - 2-hydroxypropyl methacrylate - (1-methyl-2-hydroxy)-ethyl methacrylate,
methyl methacrylate - hexyl methacrylate - 2-hydroxypropyl methacrylate - (1-methyl-2-hydroxy)ethyl methacrylate,
butyl methacrylate - 2-hydroxyethyl methacrylate,
ethyl acrylate - butyl methacrylate - hydroxypropyl methacrylate, and
butyl methacrylate - hydroxypropyl acrylate - hydroxypropyl methacrylate.

The copolymers may be obtained by various conventional polymerization processes such as, for example, in suspension, in bulk, in emulsion or in solution.

Since the nail varnishes according to the invention must be anhydrous, the polymerization is preferably carried out in solution in an organic solvent such as ethyl acetate, butyl acetate or acetone, and the like.

According to this solution polymerization process, peroxides, peresters or percarbonates are employed as a catalyst, and especially benzoyl peroxide, di-tert-butyl peroxide, tert-butylperoxy 2-ethyl hexanoate, di(4-tert-butylcyclohexyl) peroxydicarbonate or azobisisobutyronitrile.

Under certain conditions, redox systems may be employed as a polymerization initiator or the reaction mixture may be subjected to a UV irradiation in order to give rise to free radicals.

The polymerization temperature is generally between 25° and 80° C. for a period of between 30 minutes and 24 hours.

When the polymerization reaction is complete, the copolymer obtained is precipitated with a solvent in which the polymer is insoluble, such as, for example, petroleum ether or certain solvent mixtures.

The proportion of polymerization catalysts is generally between 0.25 and 5% by weight relative to the total weight of the monomers to be reacted.

A number of examples of preparation of the copolymers which can be employed in the anhydrous varnishes according to the invention will be described later in the experimental part.

The anhydrous nail varnishes according to the invention preferably contain from 3 to 35% by weight of a copolymer such as defined above, the remainder consisting essentially of the solvent system for the varnish, that is to say the usual solvents and/or diluents which are conventional in the case of a composition of this type.

The nail varnishes according to the invention additionally contain from 0.2 to 10% by weight of at least one plasticizing agent in order to improve the adhesiveness and the flexibility of the film.

The chief plasticizing agents capable of being employed in the varnishes according to the invention are: tricresyl phosphate, benzyl benzoate, tributyl phosphate, butyl acetylricinoleate, glyceryl acetylricinoleate, dibutyl phthalate, butyl glycolate, dioctyl phthalate, butyl stearate, tributoxyethyl phosphate, triphenyl phosphate, triethyl citrate, tributyl citrate, tributyl acetylcitrate, tri-2-ethylhexyl acetylcitrate, dibutyl tartrate, dimethoxyethyl phthalate, diisobutyl phthalate, diamyl phthalate, camphor, glycerol triacetate and mixtures thereof.

According to a particular embodiment of the invention, the anhydrous nail varnishes contain no resin of the aryl sulphonamide formaldehyde (Santolite) type.

The solvent system for the varnishes according to the invention is obtained by mixing various volatile organic solvents.

Among these solvents there may be mentioned acetone, ethyl acetate, butyl acetate, 2-methoxyethyl acetate, methyl ethyl ketone, methyl isobutyl ketone and methyl acetate.

The solvent system also contains a diluent which is preferably a saturated linear or branched hydrocarbon such as hexane, octane, or the like, or else an aromatic hydrocarbon such as toluene, xylene, or the like, in a proportion which is generally between 10 and 30% relative to the total weight of the varnish.

The varnishes according to the invention may also contain other volatile solvents such as ethanol, n-butanol, n-propanol, isopropanol or mixtures thereof.

The pigments of the nail varnishes according to the invention may be organic or inorganic in nature.

Among the organic pigments there may be mentioned D and C Red No. 10, 11, 12 and 13, D and C Red No. 7, D and C Red No. 5 and 6, D and C Red No. 34, lakes such as lake D and C Yellow No. 5, and lake D and C Red No. 2.

Among the inorganic pigments there may be mentioned titanium dioxide, bismuth oxychloride, brown iron oxide, red iron oxides and guanine.

In the varnish compositions according to the invention, the pigments are generally present in a proportion of between 0.1 and 8% relative to the total weight of the varnish.

Although it is possible to do completely without any products which make it possible to prevent pigment sedimentation, according to certain embodiments it is possible to employ such products as, for example, "Bentone 27" or "Bentone 38", but in proportions which are very markedly lower than those recommended hitherto, with the result that their presence has no influence whatever on the film gloss after drying.

In this embodiment, the varnish may contain between 0.3 and 1% by weight of "Bentone 27" or "Bentone 38".

According to an especially preferred embodiment of the invention, the varnishes are in the form of a two-part packaging.

The first part consists of a varnish such as defined above, but of a generally high viscosity of between 3 and 200 Pa s, but preferably between 4 and 150 Pa s (at 25° C.), and the second part consists of a polar solvent and more particularly of an alcohol such as ethanol, propanol or isopropanol, or a mixture of alcohols.

Packaging of this type makes it possible to avoid completely the use of thixotropic agents such as montmorillonite-type clays modified by an amine (Bentones).

In fact, the high viscosity of the first part of the varnish makes it possible to keep the pigments, especially titanium dioxide, in suspension so that no sedimentation occurs during the storage, which may be for a number of months before use.

The appropriate viscosity of the first part of the varnish is a function of the polymer concentration, of the concentration of plasticizing agent and of the ratio of the hydrocarbons to the esters employed to form the solvent system or mixture.

The polymer concentration is preferably between 25 and 35% and the concentration of plasticizing agent is approximately between 2 and 8%.

During use, the second part is brought into the first part in order to make the varnish sufficiently fluid by shaking and thus to allow it to be easily applied to the nails.

The fluidification is virtually instantaneous and the period for which the varnish may be stored without pigment sedimentation being observed is of the order of 1 to 4 months, which corresponds to a normal period of use of a traditional varnish.

In order to utilize this particular embodiment of the invention, it is possible, for example, to employ conventional nail varnish bottles, but in which the closure system comprises a closed cavity containing the alcohol or a mixture of alcohols.

The content of the cavity is then released by an appropriate means, for example by perforation or by squeezing, and it is mixed with the thick varnish by shaking.

The viscosity of the varnish after dilution is then between approximately 0.15 and 0.6 Pa s (at 25° C.) and this allows it to be properly spread on the nails.

According to another embodiment, it is also possible to deposit a certain quantity of thick varnish on the nail, and then a sufficient quantity of an alcohol or of a mixture of alcohols. As soon as the alcohol comes into contact with the thick varnish on the nail, the varnish becomes fluid, thus permitting a proper spreading on the nail surface.

A number of examples of the preparation of the copolymers and of examples of nail varnishes will now be given by way of illustration and without limitation of any nature being implied.

EXAMPLE I

Butyl methacrylate (60%) - hydroxypropyl methacrylate (40%) copolymer 60 g of butyl methacrylate (pure grade sold by Fluka), 40 g of hydroxypropyl methacrylate (practical grade*, sold by Fluka) and 0.25 g of azobisisobutyronitrile dissolved in 75 g of ethyl acetate are placed in a 500-cm$^3$ round-bottomed flask fitted with a mechanical stirrer, a condenser and a nitrogen inlet tube.

* The hydroxypropyl methacrylate of practical grade is a mixture of two isomers, which are 2-hydroxypropyl methacrylate and (1-methyl-2-hydroxy)ethyl methacrylate.

The reaction mixture is heated to 75° C. with stirring for 40 min. The temperature is kept at 75° C. for 8 hours and the mixture is then allowed to cool to ambient temperature. The solution is diluted with 125 g of ethyl acetate and the polymer is then precipitated by pouring the solution into 3 l of petroleum ether.

After drying, the expected polymer is obtained in an 80% yield.

Viscosity: 0.4 Pa s (in 28% solution in ethyl acetate at 25° C.).

EXAMPLE II

Butyl methacrylate (50%) - hydroxypropyl methacrylate (50%) copolymer

This polymer is prepared from the following, using the same operating procedure as that described in Example I:
50 g of hydroxypropyl methacrylate (practical grade),
50 g of butyl methacrylate (pure grade),
0.25 g of azobisisobutyronitrile, and
75 g of ethyl acetate.

When the polymerization is complete, the solution is diluted with 150 g of ethyl acetate and the copolymer is then obtained by precipitation with petroleum ether.

After drying, the expected polymer is obtained in an 85% yield.

Viscosity: 1.1 Pa s (in 28% solution in ethyl acetate at 25° C.).

EXAMPLE III

Butyl methacrylate (70%) - hydroxypropyl methacrylate (30%) copolymer

This copolymer is prepared from the following, using the same operating procedure as that described in Example I:
70 g of butyl methacrylate (pure grade)
30 g of hydroxypropyl methacrylate (practical grade)
0.25 g of azobisisobutyronitrile, and
75 g of ethyl acetate.

When the polymerization is complete, the solution is diluted with 140 g of ethyl acetate and the polymer is then precipitated in petroleum ether.

After drying, the expected polymer is obtained in a 90% yield.

Viscosity: 0.42 Pa s (in 28% solution in ethyl acetate at 25° C.).

EXAMPLE IV

Butyl methacrylate (40%) - hydroxypropyl methacrylate (60%) copolymer

This copolymer is prepared from the following, using the same operating procedure as that described in Example 1:
40 g of butyl methacrylate (pure grade)
60 g of hydroxypropyl methacrylate (practical grade)
0.25 g of azobisisobutyronitrile, and
75 g of ethyl acetate.

2 h 30 min and 3 hours after the temperature of 75° C. has been reached, 16.7 g and 33.3 g of ethyl acetate are introduced, respectively. Polymerization is allowed to continue for 8 hours in all. When the polymerization is complete, the solution is diluted with 342 g of ethyl acetate, and the polymer is then precipitated in petroleum ether. After drying, the expected polymer is obtained in a 90% yield.

Viscosity: 5.5 Pa s (in 28% solution in ethyl acetate at 25° C.).

EXAMPLE V

Methyl methacrylate (36%) - butyl methacrylate (29%) - hydroxypropyl methacrylate (35%) copolymer This copolymer is prepared from the following, using the same operating procedure as that described in Example I:
36 g of methyl methacrylate (pure grade)
29 g of butyl methacrylate (pure grade)
35 g of hydroxypropyl methacrylate (practical grade)
0.25 g of azobisisobutyronitrile, and
75 g of ethyl acetate.

4 hours after the temperature of 75° C. has been reached, 83.3 g of ethyl acetate are introduced. Polymerization is allowed to continue for 8 hours in all. When the polymerization is complete, the mixture is diluted with 300 g of ethyl acetate, and the polymer is then precipitated by pouring the solution into 4 liters of petroleum ether. After drying, the expected polymer is obtained in a 90% yield.

Viscosity: 10.2 Pa s (in 28% solution in ethyl acetate at 25° C.).

EXAMPLE VI

Ethyl acrylate (10%) - butyl methacrylate (40%) - hydroxypropyl methacrylate (50%) copolymer This copolymer is prepared from the following, using the same operating procedure as that described in Example
10 g of ethyl acrylate
40 g of butyl methacrylate
50 g of hydroxypropyl methacrylate
0.25 g of azobisisobutyronitrile, and
75 g of ethyl acetate.

When the polymerization is complete the solution is diluted with 300 g of ethyl acetate and the polymer is then precipitated with petroleum ether.

After drying, the expected polymer is obtained in an 80% yield.

Viscosity: 0.9 Pa s (in 28% solution in ethyl acetate at 25° C.).

EXAMPLE VII

Butyl methacrylate (50%) - hydroxypropyl acrylate (5%) - hydroxypropyl methacrylate (45%) copolymer This polymer is prepared from the following, using the same operating procedure as that described in Example I:

50 g of butyl methacrylate
5 g of hydroxypropyl acrylate,
45 g of hydroxypropyl methacrylate,
0.25 g of azobisisobutyronitrile, and
75 g of ethyl acetate.

When the polymerization is complete, the solution is diluted with 300 g of ethyl acetate and the polymer is then precipitated with petroleum ether. After drying, the expected polymer is obtained in an 85% yield.

Viscosity: 0.85 Pa s (in 28% solution in ethyl acetate at 25° C.).

EXAMPLES OF NAIL VARNISHES

EXAMPLE A

An anhydrous nail varnish is prepared according to the invention by mixing the following ingredients:

| | |
|---|---|
| Butyl methacrylate (60%) - hydroxypropyl methacrylate (40%) copolymer according to Example I | 20 g |
| Tributyl acetylcitrate sold under the name of "Citroflex A-4" by Pfizer | 4 g |
| Solvent mixture consisting of: | |
| toluene 33% | |
| ethyl acetate 27% | |
| butyl acetate 40% q.s. | 100 g |

In this example, the copolymer of Example I may be replaced by the same quantity of one of the copolymers prepared according to Examples II, III, VI or VII.

EXAMPLE B

An anhydrous nail varnish is prepared according to the invention by mixing the following ingredients:

| | |
|---|---|
| Butyl methacrylate (40%) - hydroxypropyl methacrylate (60%) copolymer according to Example IV | 20 g |
| Tributyl acetylcitrate | 4 g |
| Ethyl acetate q.s. | 100 g |

EXAMPLE C

A coloured anhydrous nail varnish is prepared according to the invention by mixing the following ingredients:

| | |
|---|---|
| Butyl methacrylate (60%) - hydroxypropyl methacrylate (40%) copolymer according to Example I | 20 g |
| Tributyl acetylcitrate | 4 g |
| Bentone 27 | 1 g |
| Citric acid | 0.05 g |
| Titanium dioxide | 0.3 g |
| Brown Iron oxide | 0.2 g |
| Ferric (Prussian) blue | 0.1 g |
| D and C Red 7 - calcium lake | 0.3 g |
| D and C Yellow 5 - aluminium lake | 0.7 g |
| Solvent mixture consisting of: | |
| toluene 33% | |
| ethyl acetate 27% | |
| butyl acetate 40% q.s. | 100 g |

In this example, the polymer prepared according to Example I may be replaced by the same quantity of one of the copolymers according to Examples II, III, VI or VII.

EXAMPLE D

An anhydrous nail varnish is prepared according to the invention by mixing the following ingredients:

| | |
|---|---|
| Methyl methacrylate (36%) - butyl methacrylate (29%) - hydroxypropyl methacrylate (35%) copolymer according to Example V | 17 g |
| Tributyl acetylcitrate | 5 g |
| Solvent mixture consisting of: | |
| toluene 33% | |
| ethyl acetate 27% | |
| butyl acetate 40% q.s. | 100 g |

EXAMPLE E

A nail varnish which is stable with time is prepared according to the invention by mixing the following ingredients:

| | |
|---|---|
| Butyl methacrylate (50%) hydroxypropyl methacrylate (50%) copolymer according to Example II | 25 g |
| Tributyl acetylcitrate | 5.6 g |
| Titanium dioxide | 0.3 g |
| D and C Red 34 | 0.3 g |
| Toluene | 38 g |
| Ethyl acetate | 7 g |
| Butyl acetate | 24 g |

This thick varnish forms the first part of a two-part packaging, the second part consisting of a sufficient quantity of ethanol.

When in use, a sufficient quantity of varnish is deposited on the nail and it is then spread out by means of a brush wetted in ethanol.

In this example, the copolymer according to Example II may be advantageously replaced by the copolymer according to Example V.

EXAMPLE F

A stable nail varnish is prepared according to the invention by mixing the following two parts when it is first used:

1st part

This corresponds to the thick varnish described in Example E.

2nd part

This consists of a mixture of ethanol (7.5 g) and isopropanol (7.5 g).

After homogenization by agitation, the varnish is applied to nails with a brush.

After fluidification the varnish is stable for at least 1 month.

EXAMPLE G

A stable nail varnish is prepared according to the invention by mixing the following two parts when it is first used:

1st part

| | |
|---|---|
| Methyl methacrylate (36%) - butyl methacrylate (29%) - hydroxypropyl methacrylate (35%) copolymer according to Example V | 24.49 g |
| Titanium dioxide | 0.3 g |
| D and C Red 34 | 0.3 g |
| Tributyl acetylcitrate | 5.51 g |
| Ethyl acetate | 15 g |
| Butyl acetate | 21 g |
| Toluene | 24 g |

2nd part

| | |
|---|---|
| Ethanol | 18 g |

After homogenization by agitation, the varnish is ready for use. It is stable for at least 1 month after the first use.

EXAMPLE H

A stable nail varnish is prepared according to the invention by mixing the following two parts when it is first used:

1st part

| | |
|---|---|
| Methyl methacrylate (36%) - butyl methacrylate (29%) - hydroxypropyl methacrylate (35%) copolymer according to Example V | 74.49 g |
| Titanium dioxide | 0.3 g |
| D and C Red 34 | 0.3 g |
| Tributyl acetylcitrate | 5.51 g |
| Ethyl acetate | 10 g |
| Butyl acetate | 14 g |
| Toluene | 16 g |

2nd part

| | |
|---|---|
| Ethanol | 30 g |

After homogenization by agitation, the varnish is ready for use. It is stable for at least 1 month after the first use.

EXAMPLE I

A stable nail varnish is prepared according to the invention using the procedure of Example F, but the 1st part additionally contains 1 g of Santolite MHP.

After fluidification, the varnish is stable for at least one month.

We claim:

1. Anhydrous nail varnish, free from nitrocellulose, containing 3 to 35% by weight of at least one resin in a solvent system for nail varnishes, wherein said resin is a copolymer containing units resulting from the copolymerization of a mixture consisting essentially:

(1) of 20 to 70% of at least one alkyl acrylate or methacrylate of the formula:

in which:
   R' denotes a hydrogen atom or a methyl radical, and R denotes a saturated, linear or branched hydrocarbon chain containing from 1 to 6 carbon atoms, and (2) of 30 to 80% of at least one hydroxyalkyl acrylate or methacrylate of the formula:

in which:
   $R_1$ denotes a hydrogen atom or a methyl radical and $R_2$ denotes a linear or branched hydrocarbon chain containing from 2 to 4 carbon atoms and 1 or 2 hydroxyl(s), provided that said copolymer does not contain more than 30% of units derived from the copolymerization of an alkyl acrylate and/or of a hydroxyalkyl acrylate,
   the viscosity of the copolymer at a concentration of 28% in ethyl acetate at 25° C. being higher than 0.1 Pa s.

2. Nail varnish according to claim 1, wherein the viscosity of said resin at a concentration of 28% in ethyl acetate at 25° C. is between 0.15 and 20 Pa s.

3. Nail varnish according to claim 1, wherein the copolymer contains units resulting from the copolymerization:
   (1) of 40 to 60% by weight of an alkyl acrylate or methacrylate of formula (I),
   (2) of 40 to 60% by weight of a polar monomer of formula (II).

4. Nail varnish according to claim 1, wherein the copolymer is selected from the group consisting of the following copolymers:
   butyl methacrylate - 2-hydroxypropyl methacrylate,
   butyl methacrylate - (1-methyl-2-hydroxy)ethyl methacrylate,
   butyl methacrylate - methyl methacrylate - 2-hydroxypropyl methacrylate - (1-methyl-2-hydroxy)ethyl methacrylate,
   methyl methacrylate hexyl methacrylate - 2-hydroxypropyl methacrylate - (1-methyl-2-hydroxy)ethyl methacrylate,
   butyl methacrylate - 2-hydroxyethyl methacrylate,
   ethyl acrylate - butyl methacrylate - hydroxypropyl methacrylate, and
   butyl methacrylate - hydroxypropyl acrylate - hydroxypropyl methacrylate.

5. Nail varnish according to claim 1, wherein said nail varnish contains from 0.2 to 10% by weight of at least one plasticizing agent.

6. Nail varnish according to claim 1, wherein said nail varnish contains from 0.1 to 8% by weight of at least one pigment of organic or inorganic nature.

7. The nail varnish of claim 1, wherein the molecular weight of the copolymer is from 20,000 to 1,000,000.

8. The nail varnish of claim 1, wherein the molecular weight of the copolymer is from 30,000 to 200,000.

9. The nail varnish of claim 1, wherein said varnish is suitable for use on keratin-containing nails.

* * * * *